United States Patent [19]

Mordes et al.

[11] Patent Number: 4,464,356

[45] Date of Patent: Aug. 7, 1984

[54] ANOREXIGENIC COMPOSITION AND METHOD

[76] Inventors: John P. Mordes, 80 Devonshire Rd., Waban, Mass. 02168; Aldo A. Rossini, 62 Rambling Rd., Sudbury, Mass. 01776

[21] Appl. No.: 497,630

[22] Filed: Jun. 21, 1983

Related U.S. Application Data

[63] Continuation of Ser. No. 375,877, May 7, 1982, abandoned.

[51] Int. Cl.³ .......................................... A61K 35/407
[52] U.S. Cl. .................................... 424/106; 424/95; 424/177
[58] Field of Search .......................... 424/95, 106, 177

[56] References Cited

PUBLICATIONS

Chem. Abst.—10th Collect. Index, vol. 86–95, (1977–1981), p. 13682GS.

Primary Examiner—Sam Rosen
Attorney, Agent, or Firm—William B. Walker; Donald W. Erickson

[57] ABSTRACT

A water-soluble aqueous extract obtained from a 5123 Morris Hepatoma contains an anorexigenic agent having a molecular weight of from 3500 to 10,000 Daltons.

8 Claims, No Drawings

ANOREXIGENIC COMPOSITION AND METHOD

FIELD OF THE INVENTION

This invention relates to a novel anorexigenic composition and methods for its use and manufacture. The composition is a water-soluble, polar solvent extract of a 5123 Morris Hepatoma.

The Government has rights in this invention pursuant to Grant No. 117-82 awarded by the Department of Health and Human Services.

This application is a continuation of application Ser. No. 375,877, filed May 7, 1982, now abandoned.

BACKGROUND OF THE INVENTION
DESCRIPTION OF THE PRIOR ART

Pharmacologic agents have been previously used to induce anorexia. The agents most commonly used are the amphetamines including dextroamphetamine, benzphetamine, diethylpropion and phenmetrazine. These compounds are indirectly acting sympathomimetic agents, effecting release of norepinephrine, causing a wide variety of peripheral side effects and always risking drug dependency. There are generally no anorectic agents currently available for treatment of obesity which are generally regarded as both efficacious and safe.

The presenting symptom of cancer is often decreased appetite and weight loss. The weight loss cannot be accounted for by the tumor burden. It has been suggested that tumor induced anorexia may represent a paraneoplastic syndrome mediated by a circulating substance by A. Theologides, "Anorexia-producing Intermediary Metabolite", *J. Clin. Nutr.* 29, 552–558 (1976) and W. D. Odell et al, "Humoral Syndrones Associated with Cancer," *Ann. Rev. Med.* 29, 370–406 (1978). However, such a theory has not been heretofore substantiated.

SUMMARY OF THE INVENTION

This invention relates to a method for reducing the appetite of a mammal comprising administering an appetite suppressing amount of a water-soluble extract of a 5123 Morris Hepatoma, and preferably administering a fraction thereof which has been purified. The anorexigenic compositions and the processes for manufacturing them are also aspects of this invention.

The process for preparing the purified anorexigenic fraction obtained from the 5123 Morris Hepatoma comprises (a) extracting an acidic, aqueous homogenate of a 5123 Morris Hepatoma with a non-polar lipophilic solvent, separating the aqueous phase, and removing the solvent from the aqueous phase to yield an initial residue, and (b) purifying an aqueous extract of the initial residue to yield a purified fraction thereof.

DETAILED DESCRIPTION OF THE INVENTION

The anorexigenic agent of this invention is obtained from the 5123 Morris Hepatoma which is available from the tumor bank maintained by the Mason Research Institute 57 Union Street, Worcester, Mass. 01608. This is a tumor which can be serially transplanted in Buffalo rats. The tumor is preferably harvested when about 2 cm by 5 cm in size. Immediately following removal from the rats, the tumors are immersed in liquid nitrogen and stored at $-40°$ C. until they are processed.

The tumors are first homogenized by standard procedures for disrupting cellular tissue. For example, they can be homogenized in dilute cold aqueous hydrochloric acid solution and then further homogenized after adding acetone. The solids are removed by centrifugation yielding an aqueous solution or dispersion. The latter is extracted with a lipophilic non-polar solvent to separate undesirable constituents from the aqueous phase, and the aqueous phase is separated and then preferably frozen and lyophilized.

The lyophilized residue can be treated to remove residual insoluble material by resuspending it in water, centrifuging it, and lyophilizing the supernatant to yield an extract residue having anorexic activity.

Further purification to separate the active constituent from inactive components can be achieved by conventional gel chromatography using a standard hydrophilic gel column. Examples of suitable hydrophilic gels include the polydextran gels such as SEPHADEX (sold by Pharmacia, Uppsala, Sweden), polyacrylamide gels such as BIO-GEL (Prepared by Bio-RAD Laboratories, Richmond, Calif.) and the aqueous or agar gels such as SEPHAROSE (Pharmacia). An aqueous extract of the extract residue is acidified to a pH of 1.5 to 5.0 and preferably from 2 to 3. The acidified extract is applied to the gel column and eluted with water acidified to a pH of 1.5 to 5.0, preferably from 2 to 3. The acidifying agent is preferably a water-soluble aliphatic acid such as acetic acid.

The eluate fractions are collected, and the active fractions identified by examination for optical density at a frequency of $280\mu$ using a standard spectrophotometer such as a Guilford Spectrometer (Model 240). The first fractions having an optical density of 1.6 or greater are separated and pooled. The optical density of fractions subsequently obtained will fall below this level and nothing thereafter should be retained.

The active fractions are then cooled and the solvent is removed, for example by lyophilization, to yield an active concentrate.

This concentrate can be administered parenterally, orally using an enteric coating, sublingually, rectally or by other standard procedures. For parenteral administration, the active material is preferably dispersed at a concentration of from 100 to 300 mg per liter in an isotonic solution suitable for parenteral injection.

This invention is further illustrated by the following specific but non-limiting examples. The examples are descriptions of actual experiments unless otherwise indicated.

EXAMPLE 1

The extraction procedure for the Morris Hepatoma was as follows. The tumor was harvested when the subcutaneous tumors in rats achieved a size of about 2 cm by 5 cm. The rats were killed in an atmosphere of 100% $CO_2$. The tumors were immediately extirpated and then immersed in liquid nitrogen. After freezing, the tumors were kept at $-40°$ C. until use.

The tumor was extracted in 250 gm lots. The frozen preweighed tumor was added to 500 ml of 0.5N cold HCl and homogenized for 90 sec. Then 2 liters of acetone were added to the mixture, and the mixture was homogenized for an additional 120 sec. The resultant mixture was centrifuged at 2,000 rpm for 45 minutes. The supernatant was then extracted twice with 4 liters of petroleum ether. The aqueous phase was separated and reduced in volume to 1500 ml, frozen, and lyophilized.

EXAMPLE 2

For purification using gel filtration, 8 lots of 250 mg of tumor were prepared. Approximately 100 g of initial lyophilized residue (5% yield) was obtained. This residue was resuspended in distilled water to a concentration of 0.2 gm/ml. This suspension was centrifuged at 10,000 rpm for 15 minutes. The supernatant pH was then adjusted to 2.5 with 8M NaOH and recentrifuged at 10,000 rpm for 15 min. The supernatant was then applied to an 18 liter SEPHADEX G-25 column run with 0.2M acetic acid, pH 2.5. 35 Fractions of 500 ml each were collected and stored at 5° C. Seven pools were tested for bioactivity.

| Pool | Fractions |
|---|---|
| 1 | 1–5 |
| 2 | 6–10 |
| 3 | 11–15 |
| 4 | 16–20 |
| 5 | 21–25 |
| 6 | 26–30 |
| 7 | 31–35 |

EXAMPLE 3

The residue obtained in Example 1 was tested in a bioassay system which was established as follows. Twenty-four rats housed in individual metal hanging cages on a rack were kept in a small windowless room. The light cycle was reversed, such that the rats experienced darkness from 9 a.m. to 9 p.m. Since rats are nocturnal feeders, this arrangement allowed study of the rats during their usual feeding period. The rats were allowed water continuously ad libitum, but were given food (a balanced Purina rat chow in powder form) only from 9 a.m. to noon. The food was in 16 oz glass jars with a 3 cm opening in the lid to minimize spillage. This arrangement allowed for rapid determination of food intake by weighing the jars. Within a week of being placed on a 3-hours-a-day of food regimen, most 200 g rats stabilized at a food intake of 12 to 16 gm food per 3 hour feeding period. They maintained their weight on this regimen, but did not grow. This sensitive bioassay system thus permitted the detection of small but significant anorectic activity, for it tested food consumption in rats fasted for 21 hours and trained to eat voraciously when offered food.

The anorectic activity of the crude extract was determined in the bioassay as follows. In all experiments described hereafter, Day "0" refers to the day on which the injection was administered. Days −1 and +1 are the preceeding and following days respectively. All data refer to grams of food eaten during the 3 hours of feeding, The results obtained at 2 doses with saline as a control:

| | | DAYS | | |
|---|---|---|---|---|
| | N | −1 | 0 | +1 |
| GROUP I[a] | 4 | 10.9 ± 1.1 | 5.2 ± 2.6 | 5.8 ± 0.7 |
| GROUP II[b] | 4 | 10.8 ± 1.1 | 9.2 ± 0.5 | 6.6 ± 0.2 |
| GROUP III[c] | 3 | 11.2 ± 0.6 | 11.0 ± 5.7 | 6.3 ± 1.2 |

[a] 105 mg crude extract/rat, 3 cc, pH 7.0, 463 mOsm/kg
[b] 50 mg crude extract/rat, 3 cc, pH 7.0, 284 mOsm/kg
[c] 3 cc normal saline/rat, pH 7.0, 300 mOsm/kg (control)

From these data it can be concluded that anorexigenic bioactivity was present in the extract of Morris Hepatoma. Further, since the extracted material was soluble in 75% acetone, it can also be concluded that the molecular weight of the extracted anorexigenic material is likely to be less than approximately 10,000 Daltons.

EXAMPLE 4

Repeating the procedure of Example 3 with residue of the purified fractions obtained in Example 2, the results shown in the following table were obtained:

| Pool | pH | mOsm/kg | N | −1 | 0 | +1 |
|---|---|---|---|---|---|---|
| 1 | 4.90 | 232 | 5 | 12.7 ± 2.3 | 1.2 ± 0.8 | 5.8 ± 1.4 |
| 2 | 5.40 | 267 | 4 | 13.2 ± 1.7 | 7.1 ± 1.3 | 10.7 ± 1.2 |
| 3 | 5.65 | 272 | 4 | 13.8 ± 2.9 | 6.9 ± 3.0 | 9.3 ± 1.9 |
| 4 | 4.98 | 360 | 4 | 10.7 ± 1.2 | 6.4 ± 1.3 | 9.2 ± 1.5 |
| 5 | 5.11 | 325 | 5 | 8.9 ± 2.0 | 8.0 ± 1.1 | 8.7 ± 1.6 |
| 6 | 5.66 | 349 | 5 | 12.0 ± 2.0 | 10.7 ± 0.6 | 8.9 ± 2.0 |
| 7 | 5.14 | 287 | 4 | 9.3 ± 1.9 | 9.6 ± 1.2 | 9.1 ± 1.2 |
| Saline | 4.94 | 278 | 4 | 13.5 ± 1.2 | 8.8 ± 1.6 | 9.3 ± 1.4 |
| Saline | 5.02 | — | 4 | 9.3 ± 1.4 | 10.9 ± 1.9 | 10.0 ± 0.5 |

From these data it can be seen that anorexigenic activity as measured in the bioassay system is very high and is far greatest in the first pool of fractions. This pool had an optical density greater than 1.6 measured at a frequency of 280μ, indicating a distinct, early protein peak.

The invention claimed is:

1. Method for reducing appetite in a mammal comprising administering an appetite suppressing dose of an aqueous extract of a 5123 Morris Hepatoma.

2. The method of claim 1 wherein the extract has been purified.

3. The method of claim 1 comprising injecting an aqueous, isotonic dispersion of an aqueous extract of a 5123 Morris Hepatoma.

4. The method of claim 3 wherein the aqueous extract has been purified.

5. An anorexigenic composition consisting essentially of an aqueous extract of a 5123 Morris Hepatoma.

6. The composition of claim 5 wherein the aqueous extract has been purified.

7. A process for preparing the composition of claim 6 comprising
   (a) extracting an acidic aqueous homogenate of 5123 Morris Hepatoma with a non-polar, lipophilic solvent, separating the aqueous phase and removing water from the aqueous phase to yield an initial residue, and
   (b) purifying an aqueous solution extract of the initial residue by gel chromatography.

8. The anorexigenic product of the process of claim 7.

* * * * *